(12) United States Patent
Scheckel et al.

(10) Patent No.: US 11,617,876 B2
(45) Date of Patent: Apr. 4, 2023

(54) DRIVE SHAFT COVER WITH A HEAT CONDUCTING PART

(71) Applicant: ECP ENTWICKLUNGSGESELLSCHAFT MBH, Charlottenburg (DE)

(72) Inventors: Mario Scheckel, Berlin (DE); Robert Decke, Berlin (DE); Joerg Schumacher, Teltow (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 318 days.

(21) Appl. No.: 16/641,169

(22) PCT Filed: Aug. 22, 2018

(86) PCT No.: PCT/EP2018/072698
§ 371 (c)(1),
(2) Date: Feb. 21, 2020

(87) PCT Pub. No.: WO2019/038343
PCT Pub. Date: Feb. 28, 2019

(65) Prior Publication Data
US 2020/0197585 A1    Jun. 25, 2020

(30) Foreign Application Priority Data
Aug. 23, 2017  (EP) ..................... 17187607

(51) Int. Cl.
*A61M 25/085*  (2006.01)
*A61M 60/422*  (2021.01)
(Continued)

(52) U.S. Cl.
CPC .......... *A61M 60/422* (2021.01); *A61M 60/13* (2021.01); *A61M 60/216* (2021.01);
(Continued)

(58) Field of Classification Search
CPC .............. A61M 60/857; A61M 60/422; A61M 60/818; A61M 60/205; A61M 60/135; A61M 2205/0211; A61M 2205/0233
(Continued)

(56) References Cited

U.S. PATENT DOCUMENTS 7,011,620 B1 *  3/2006  Siess ................... A61M 60/818
                                                       600/16
2013/0303970 A1 * 11/2013  Keenan ............... A61M 60/818
                                                       604/9
(Continued)

FOREIGN PATENT DOCUMENTS

EP       0364293 A2   4/1990
EP       2047873 A1   4/2009
(Continued)

OTHER PUBLICATIONS

International Search Report and Written Opinion for Application No. PCT/EP2018/072698 dated Nov. 8, 2018.
(Continued)

*Primary Examiner* — Erin M Piateski
(74) *Attorney, Agent, or Firm* — Botos Churchill IP Law LLP

(57) ABSTRACT

The application relates to a catheter device with a distal bearing for bearing a distal end of a drive shaft. The distal bearing comprises a heat conducting part for enabling heat transfer away from the distal bearing and/or a spiral sleeve for receiving the distant end of the drive shaft.

52 Claims, 7 Drawing Sheets

(51) Int. Cl.
  *A61M 60/825* (2021.01)
  *A61M 60/416* (2021.01)
  *A61M 60/13* (2021.01)
  *A61M 60/216* (2021.01)
(52) U.S. Cl.
  CPC ........ *A61M 60/416* (2021.01); *A61M 60/825* (2021.01); *A61M 2205/0211* (2013.01); *A61M 2205/0233* (2013.01)
(58) Field of Classification Search
  USPC .......................................................... 600/16
  See application file for complete search history.

(56) References Cited

U.S. PATENT DOCUMENTS

| | | | | |
|---|---|---|---|---|
| 2014/0148638 | A1* | 5/2014 | LaRose | A61M 60/824 600/16 |
| 2015/0328382 | A1* | 11/2015 | Corbett | A61M 60/865 600/16 |
| 2016/0256620 | A1 | 9/2016 | Scheckel et al. | |
| 2019/0282741 | A1* | 9/2019 | Franano | A61M 60/857 |

FOREIGN PATENT DOCUMENTS

| | | | | |
|---|---|---|---|---|
| EP | 2868331 | A2 | 5/2015 | |
| GB | 2504175 | A | 1/2014 | |
| JP | 2003515392 | A | 5/2003 | |
| JP | 2016538982 | A | 12/2016 | |
| JP | 2017515581 | A | 6/2017 | |
| WO | 2006051023 | A1 | 5/2006 | |
| WO | WO-2015063281 | A * | 5/2015 | ..... A61B 17/320758 |
| WO | 2015175718 | A1 | 11/2015 | |
| WO | 2016146659 | A1 | 9/2016 | |

OTHER PUBLICATIONS

Written Opinion of Intellectual Property Office of Singapore in corresponding application No. 11202001141X dated Mar. 11, 2021, 8 pp.
Office Action from corresponding Chinese Patent Application No. 2018800549087 dated May 6, 2022 (24 pages).
Office Action from corresponding Indian Patent Application No. 202037009349 dated Feb. 25, 2022 (6 pages).
Office Action for corresponding JP Application No. 2020-511482 dated Aug. 23, 2022 (12 pages).

* cited by examiner

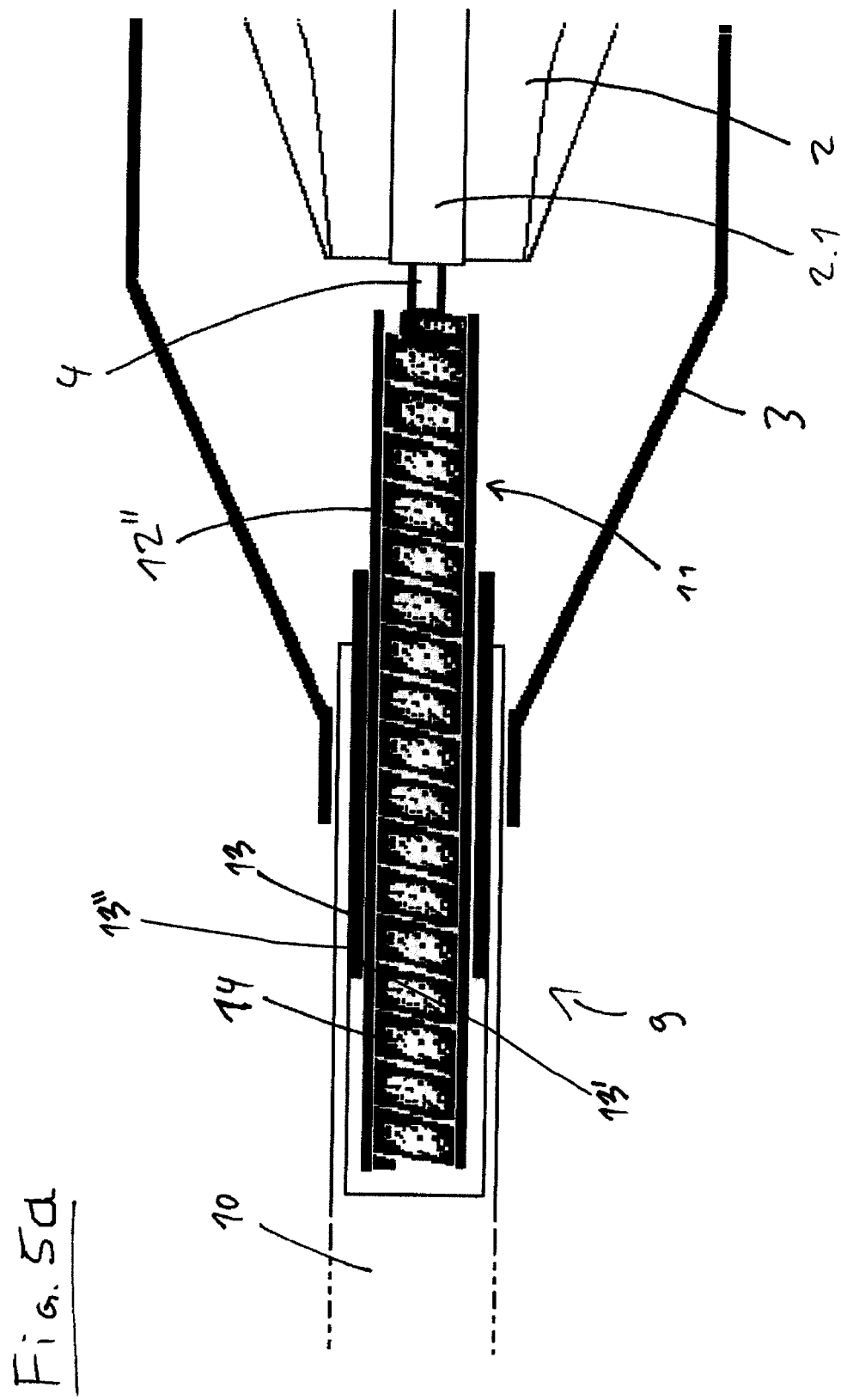

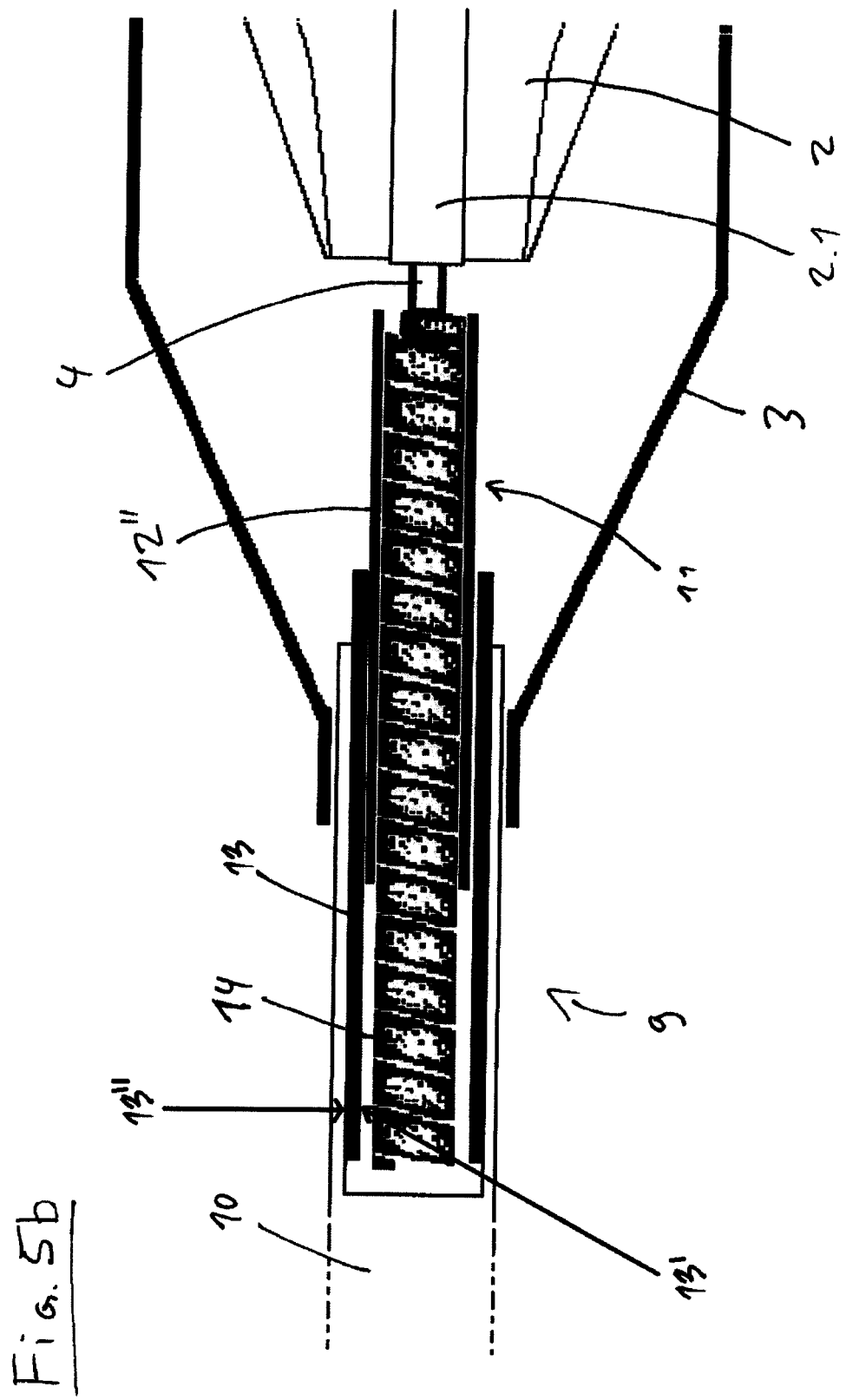

Fig. 6
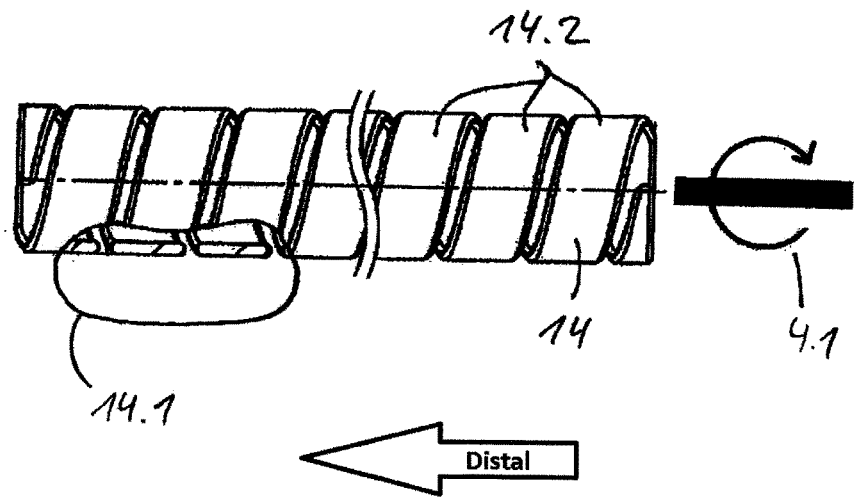
Fig. 7
(a) 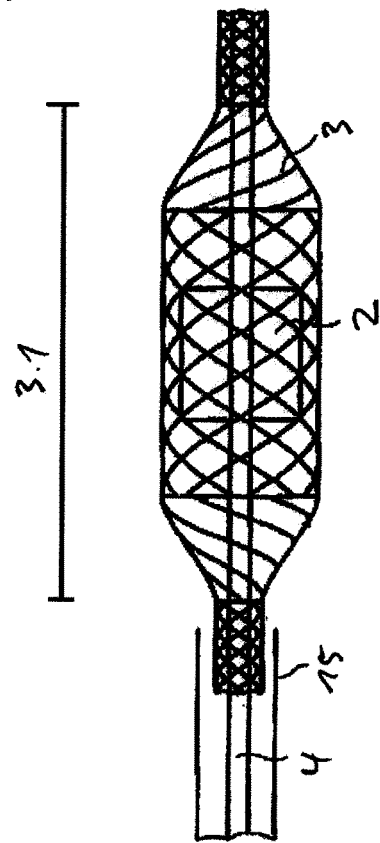   (b) 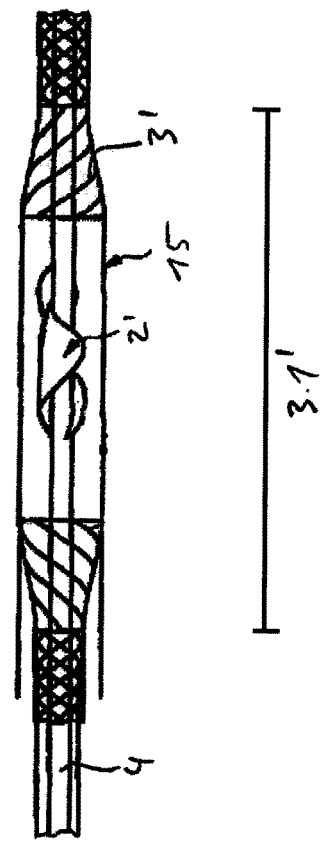

DRIVE SHAFT COVER WITH A HEAT CONDUCTING PART

CROSS-REFERENCE TO RELATED APPLICATIONS

This application is a United States National Stage filing under 35 U.S.C. § 371 of International Application No. PCT/EP2018/072698, filed Aug. 22, 2018, which claims priority to European Patent Application No. 17187607.1, filed Aug. 23, 2017. The contents of each of each of the foregoing applications are hereby incorporated by reference in their entirety. International Application No. PCT/EP2018/072698 was published under PCT Article 21(2) in English.

The application relates to a catheter device with a rotor, comprising a drive shaft, according to the preamble of the main claim.

Such catheters are typically used as blood pump arrangements, where the device is positioned in the body of a human or animal, to produce or transmit a torque or rotation movement, such that the rotor effects a flow of blood. The drive shaft runs axially along the longitudinal extension of the catheter between a driving region of the catheter and a distal end region of the catheter. Typically, the driving region is located in a proximal end region, which remains outside the body and is connected to a drive motor. Therefore, the drive shaft should remain pliable and flexible, also under load.

For many applications, it is necessary to guide the catheter along a desired path through the body, for example, along or within blood vessels, in order to position the rotor located at the distal end of the catheter at a desired location within the body, for example, within a heart ventricle of near a heart ventricle, for the duration of the respective application. The rotor and drive shaft then rotate in a rotating direction, according to the desired application, for example, such that a flow of blood from away from the patient's heart, in a proximal direction, is effected. In order to guide the catheter through a lumen, the catheter device can be designed as an expandable pump, where the rotor is designed as a radially compressible rotor, which can be arranged inside a radially compressible housing. Both the rotor and the housing can be transferred into a cannula, which is typically located proximally of the rotor and has an inner diameter that is smaller than the diameter of the rotor and the housing in an expanded state. For example, by exerting a pulling force on a pliable sheath provided around the drive shaft at the proximal end of the catheter device, the compressible rotor and the compressible housing can be transferred at least in part into the cannula, and are thereby compressed.

For example, for delivering blood, it can be necessary to produce rotation speeds of more 10,000, more than 20,000 or even more than 30,000 revolutions per minute. Often, the rotation movement must be produced over a longer period of time, such as for several days or even weeks.

For some arrangements, the provision of a distal bearing for stabilizing the distal end of the drive shaft has benefits. In some embodiments, the distal bearing can comprise an elongated polymer part wherein the drive shaft is mounted. The polymer part can for instance be made of Pebax® or Polyurethane. Furthermore, additional bearings, for instance made of ceramics, can be provided inside the elongated polymer part.

Typically, catheter devices of this type comprise a flexible atraumatic tip to avoid damage to the patient's tissue. The atraumatic tip can be made of a flexible medical grade polymer such as Pebax® or Polyurethane. Preferably, the flexible atraumatic tip is designed as a pigtail.

In some embodiments, the elongated polymer end part and the flexible atraumatic polymer tip form a single polymer end part.

Particularly high demands are placed on the mechanical and the chemical loadability of the catheter, the drive shaft, and in particular the distal bearing, which can be in contact with the rotating shaft and can therefore be subject to physical forces leading to heavy abrasive wear. At high rotational speeds, frictional heat is produced, in some cases leading to temperatures of over 160° C., thus exceeding the melting point of some medical-grade polymers used for making the above-mentioned polymer end part. Under these circumstances, a distal bearing made of such a material would be subject to melting.

Material fatigue and damaging processes on the drive shaft and the distal bearing and on other components should only progress as slowly as possible, and moreover as predictably and as controllably as possible, as they not only damage the catheter device, but also present a health hazard to the patient, as wear debris is transferred to the blood and into the patient's body. The risk of tearing and breakage of the drive shaft or the distal bearing or melting of the distal bearing should be minimized. In particular, the bearing should be designed to minimize friction and heat production, which are important factors leading to wear and tear.

Frictional forces and heat production are not only damaging to the pump itself. It should also be taken into account that blood consists of a number of constituents, such as blood cells, which can be damaged both mechanically when in contact with the rotor and the shaft or other parts of the catheter device, or thermally when exposed to the heat produced within the catheter device, for instance due to denaturation.

Furthermore, damage to patient tissue caused by the rotating elements should be avoided. For example, intraventricular pumps can cause damage to the heart, as heart tissue, such as for instance tendinous chords or structures pertaining to the mitral valve, can be sucked into the pump or become entangled with rotating parts.

To avoid entanglement of tissue with rotating parts, EP 2047873 describes Polyurethane drive shaft covers which separate the rotating drive shaft from the blood. For this purpose, the gap between the drive shaft and the drive shaft cover is kept very small. However, this can lead to increased wear and tear, especially when flexible drive shafts made out of metal are used. On the other hand, a rigid tube-shaped drive shaft cover requires precise centering of the flexible drive shaft inside the drive shaft cover. EP 2868331 describes a flexible pump, which tolerates bending of the pump head.

However, in a device as described in EP 2868331, in particular in conjunction with a flexible polymer end part at the distal end of the pump head, a rigid drive shaft cover can lead to a kink in the drive shaft upon bending of the catheter device. In particular, a kink can form in the region between the rigid drive shaft cover and the rotor, potentially leading to severe damage of the drive shaft.

In such a configuration, friction leads to relevant heat production between the drive shaft and the bearing, in some cases causing both damage to the blood and melting of the plastic of the pigtail tip. While the heat quantity deposited is not particularly large, it is very concentrated in a small area. The resulting energy density is therefore significant and leads to localized high temperatures.

The aim of the application is to address the above-mentioned problems, at least to address one or more of the following points:

- Avoiding damage to the surrounding tissue by the rotating parts of the pump, in particular in the distal end region,
- providing sufficient flexibility to allow for bending of the pump head without producing a kink in the drive shaft,
- providing sufficient resistance to wear and tear and to reduce or avoid transfer of wear debris to the patient's body,
- allowing for a flexible plastic tip at the distal end of the pump, such as a pigtail tip,
- allowing for heat transfer of the generated frictional heat to the surrounding blood to avoid local overheating.

This can be achieved by catheter devices according to the independent claims. Advantageous embodiments are given by the dependent claims and the examples provided in the description.

Catheter devices according to the application can comprise a drive shaft, which is made up of a plurality of coaxial windings, preferably with different winding directions, particularly preferably with alternating winding directions, running spirally around a cavity extending axially along the drive shaft. For example, a drive shaft can comprise two coaxial windings, with opposite winding directions, and an outer diameter of the drive shaft can lie between 0.4 mm and 2 mm, preferably lies between 0.6 mm and 1.2 mm, particularly preferably between 0.8 mm and 1.0 mm.

In the distal end region, the drive shaft is in some embodiments reinforced by a reinforcement element, for example a metal wire or a carbon wire, that is provided in the cavity extending axially along the drive shaft. In one embodiment, the reinforcement element extends from an area near the proximal end of the rotor housing, in particular from a proximal bearing configuration of the rotor housing to the distal end of the drive shaft. In one embodiment the metal wire is made of 1.4310 stainless steel.

In one embodiment, the distal bearing of such a catheter device comprises a drive shaft cover which can be provided around the drive shaft distally of the rotor. The drive shaft cover can comprise a flexible tube, for instance made of a flexible material such as silicone, Pebax®, PU or PET. The drive shaft can be rotatably mounted inside the drive shaft cover. In one embodiment, the flexible tube of the drive shaft cover is a shrink hose. The flexible tube of the drive shaft cover can be provided on the outside of the polymer end part, extending beyond the polymer end part proximally of the polymer end part. Alternatively or additionally, a flexible tube of the drive shaft cover is provided in part inside the polymer end part, extending beyond the polymer end part proximally of the polymer end part. As the drive shaft bends during operation, the drive shaft cover is sufficiently flexible to avoid a kink in the drive shaft between the drive shaft cover and the rotor.

In one embodiment, the drive shaft cover further comprises a spiral sleeve on the inside of the flexible tube for bearing the drive shaft. The spiral sleeve supports the flexible tube of the drive shaft cover from the inside, while ensuring flexibility. With such a spiral sleeve, friction between the drive shaft and the drive shaft cover, as well as wear and tear on the drive shaft cover, can be reduced.

In another embodiment, the drive shaft cover comprises a heat conducting part, or several heat conducting parts, designed to conduct heat away from the drive shaft and/or conduct heat away from the distal bearing. For instance, the heat conducting part can be configured to transfer heat to the blood of the patient during operation and/or to distribute the heat to avoid local hotspots.

The heat conducting part or the heat conducting parts have an inner side, facing the drive shaft, and an outer side, facing away from the drive shaft.

The heat conducting part is preferably designed as a tube surrounding the drive shaft. The heat conducting part can for example also be designed as one or more metal plates or tongues which are provided near the drive shaft.

The spiral sleeve and the heat conducting part or tube can each be provided in separate embodiments, for instance in conjunction with a flexible tube. An embodiment featuring both a spiral sleeve and a heat conducting part designed as a tube can be particularly advantageous.

The spiral sleeve can for example be provided in conjunction with a heat conducting part, both with or without the flexible tube. For instance, the spiral sleeve can be arranged at least in part inside the heat conducting part designed as a tube, typically extending out of the tube.

The spiral sleeve can for instance be made of round wire or it can be made of flat tape with a winding. The drive shaft is then also rotatably mounted within the spiral sleeve. The bearing spiral sleeve is preferably made of metal, for instance made of MP35N® or 35NLT®, or made of ceramics. The bearing spiral sleeve ensures the flexibility of the drive shaft cover to tolerate bending of the pump head, thus avoiding a kink between the distal bearing and the rotor, and providing sufficient resistance to wear and tear. In one embodiment, the flexible tube is provided around the full length of the spiral sleeve. In one embodiment, the flexible tube is provided only around a proximal portion of the spiral sleeve. In one embodiment, the flexible tube is provided around the outside of a portion of the polymer end part and around a portion of the spiral bearing extending out of the polymer end part.

Alternatively, an embodiment of multiple metal rings instead of a spiral is possible, preferably arranged with gaps between the rings. Preferably the rings or the sleeve are made of flat tape. The rings can be made of the same material as the spiral sleeve described above.

A spiral sleeve or rings for bearing a drive shaft have an inner diameter ranging between 0.4 mm and 2.1 mm, preferably between 0.6 mm and 1.3 mm, particularly preferably between 0.8 mm and 1.1 mm. The tape forming the spiral sleeve or rings has a thickness between 0.05 mm and 0.4 mm. The tape forming the spiral sleeve or the rings can for instance have a width between 0.4 and 0.8 mm. The gap between the rings or between the windings can for instance be between 0.04 mm and 0.2 mm.

The winding slope of the spiral sleeve and the thickness of the flexible tube, which influence the flexibility of the drive shaft cover, are preferably chosen such that the rotor can be kept at the desired position upon bending of the catheter device.

The thickness of the flexible tube can be between 5 μm and 100 μm, preferably between 10 μm and 50 μm.

In one embodiment, the inner diameter of the spiral sleeve or rings is chosen to be between 0.01 mm and 0.08 mm larger than the outer diameter of the drive shaft, preferably between 0.01 mm and 0.05 mm, for mounting the drive shaft rotatably and avoiding vibrations, while allowing at most small amounts of blood to enter the gap region.

In one embodiment, the proximal end of the spiral sleeve or rings, is located close to the rotor in the expanded state. For instance, the proximal end of the spiral sleeve or rings can be designed to have a distance of between 0.2 mm and 0.7 mm from the rotor in the expanded state, preferably a distance between 0.25 mm and 0.4 mm, to avoid that the rotor touches the drive shaft cover or spiral sleeve during operation.

Preferably, the flexibility of the drive shaft cover is such that upon bending of the pump head, the drive shaft and the rotor remain centered within the flexible housing, to avoid that the rotor touches the flexible housing during operation.

In one embodiment, a hub of the rotor extends less than 0.5 mm past the rotor blades in the distal direction, in order to be able to bring the rotor blades closer to the distal bearing without the hub potentially touching parts of the distal bearing. Preferably, it extends less than 0.1 mm in distal direction past the rotor blades, particularly preferably the hub does not extend at all past the rotor blades on the distal side.

In one embodiment, the winding direction of the spiral sleeve, when following the winding of the sleeve in the distal direction, when looking from the proximal end to the distal end of the bearing sleeve, is the opposite direction of a preferred rotating direction of the drive shaft, when looking along the drive shaft towards the distal end of the drive shaft, such that a tapered or pointed end of the spiral sleeve would not damage a rotor rotating in the preferred rotating direction if the rotor touches the spiral sleeve in the event of failure. The preferred winding direction can be the same direction as the winding direction of the outermost coaxial winding of the drive shaft or it can be the opposite direction from the winding direction of the outermost coaxial winding of the drive shaft.

The ends of the spiral sleeve are preferably face ground and the edges, at least the edges of both ends, are rounded and smooth, preferably with a ten-point mean roughness $R_z$ of $R_z \leq 2$ μm, according to the ISO 1302 standard.

Preferably, the spiral sleeve is arranged in such a manner, that, if a force is exerted at the proximal end of the catheter device to transfer the rotor and the housing into a cannula under compression, such that a relative motion of the drive shaft with respect to the distal bearing and therefore the spiral sleeve is effected, the distal end of the drive shaft remains within the distal bearing, i.e., depending on the embodiment, the distal end does not escape the drive shaft cover, the spiral sleeve, the ceramic bearing or the heat conducting tube.

In one embodiment, an additional ceramic bearing is provided within the distal bearing, located distally of the spiral sleeve.

As mentioned earlier, the catheter device can comprise a heat conducting part or tube in addition to the spiral bearing or the catheter device can comprise a heat conducting part or tube solely in combination with a bearing.

If the heat conducting part or tube is provided without the spiral bearing, a ceramic bearing, for example a ring bearing, can be provided inside the distal bearing.

If the heat conducting part or tube is provided in addition to the spiral sleeve, it can be provided around at least a portion of the spiral sleeve.

The heat conducting part or tube can lie in part within the polymer end part and in part outside of the polymer end part. Thus, heat transfer from within the distal bearing to the blood of the patient is enabled. In one embodiment, the heat conducting part or tube extends between 0.5 mm and 2 mm out of the polymer end part, preferably between 1 mm and 1.5 mm.

The flexible tube of the drive shaft cover can be provided around the spiral bearing on the inside of the heat conducting part or tube. Then, an outer side of the heat conducting part or tube can be brought in direct contact with the blood of the patient.

The flexible tube can also be provided around the outside of a portion of the polymer end part, the outside of a portion of the heat conducting part or tube extending out of the polymer end part, and a portion of the spiral sleeve that extends beyond the heat conducting part or tube. In the latter configuration, the part of the heat conducting part or tube, which extends out of the polymer end part, cannot be brought in direct contact with the blood. Rather, the flexible tube is in direct contact with the blood. In this configuration, heat is also transferred from the heat conducting part or tube to the blood, through the thin walls of the flexible tube.

The heat conducting part or tube can also lie entirely within the polymer end part, such that the heat is redistributed within the distal bearing and conducted away from the spiral bearing or the rings.

The heat conducting part or tube is for instance made of a medical grade stainless steel, such as 1.4441 stainless steel, and possesses a higher thermal conductivity than the polymer end part or the ceramic bearing.

An inner diameter of the heat conducting part designed as a tube can lie between 0.5 mm and 2.6 mm, preferably between 0.7 mm and 1.8 mm, particularly preferably between 0.9 mm and 1.6 mm.

The thickness of the heat conducting part or tube can be between 0.05 mm and 0.5 mm.

The section of the outer surface of the heat conducting part or tube which is configured to be in contact with the blood of a patient is preferably smooth.

In one embodiment, the ten point mean roughness $R_z$ according to the ISO 1302 standard in said section or portion of the outer surface of the heat conducting part is $R_z \leq 1.2$ μm.

In one embodiment, the inner side of the heat conducting part or tube is configured to be glued to the spiral sleeve. To facilitate gluing the inner side of the heat conducting part or tube to the spiral sleeve, the inner side of the part or tube can be rough. For instance, the arithmetic average surface roughness of the inner side of the heat conducting part or tube can have an average surface roughness $R_a$ according to the ISO 1302 standard of $R_a \geq 0.8$ m.

In one embodiment, the inner diameter of the heat conducting part designed as a tube is chosen to be between 0.04 mm and 0.1 mm larger than the outer diameter of the spiral sleeve or the rings so that glue can be applied in the gap.

Such catheter pumps with a heat conducting part or tube can result in shifting of the temperature hot-spot. For example, the hot spot can be shifted from a region of the drive shaft that lies inside the polymer end part to a closer to the proximal end of the polymer end part, or to a region which lies outside of the polymer end part. Such a setup can also result in a lower maximum temperature, for example a maximum temperature which is between 20° C. and 60° C. lower than the maximum temperature in a setup without heat conducting-part. In particular, the maximum temperature at the hotspot can be kept below the melting point of Pebax® or other medical grade polymers.

It is also possible to provide a catheter device which features a heat conducting part or tube as presented here, but where the distal bearing does not feature a spiral sleeve or rings.

Aspects and embodiments of the catheter device according to the application are exemplified in FIGS. 1 to 7.

Figure 4A:
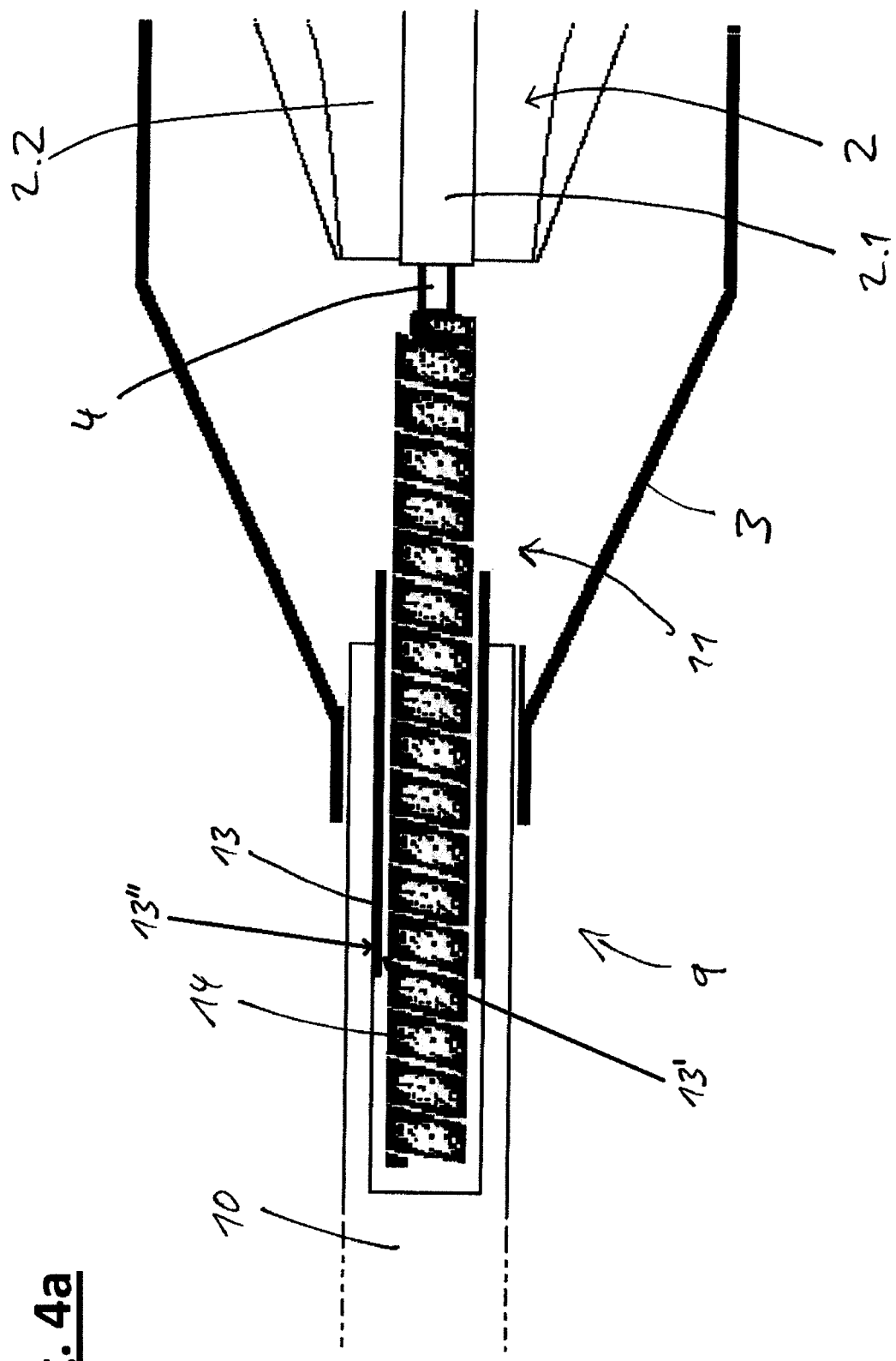

FIGS. 4a and b show schematic sketches of a section of the distal end region of a catheter device;

FIGS. 5a and b show schematic sketches of a section of the distal end region of a catheter device;

FIG. 6 shows the spiral sleeve; and

FIG. 7 shows the rotor and the rotor housing in the expanded state (a) and in the compressed state (b).

Figure 1:
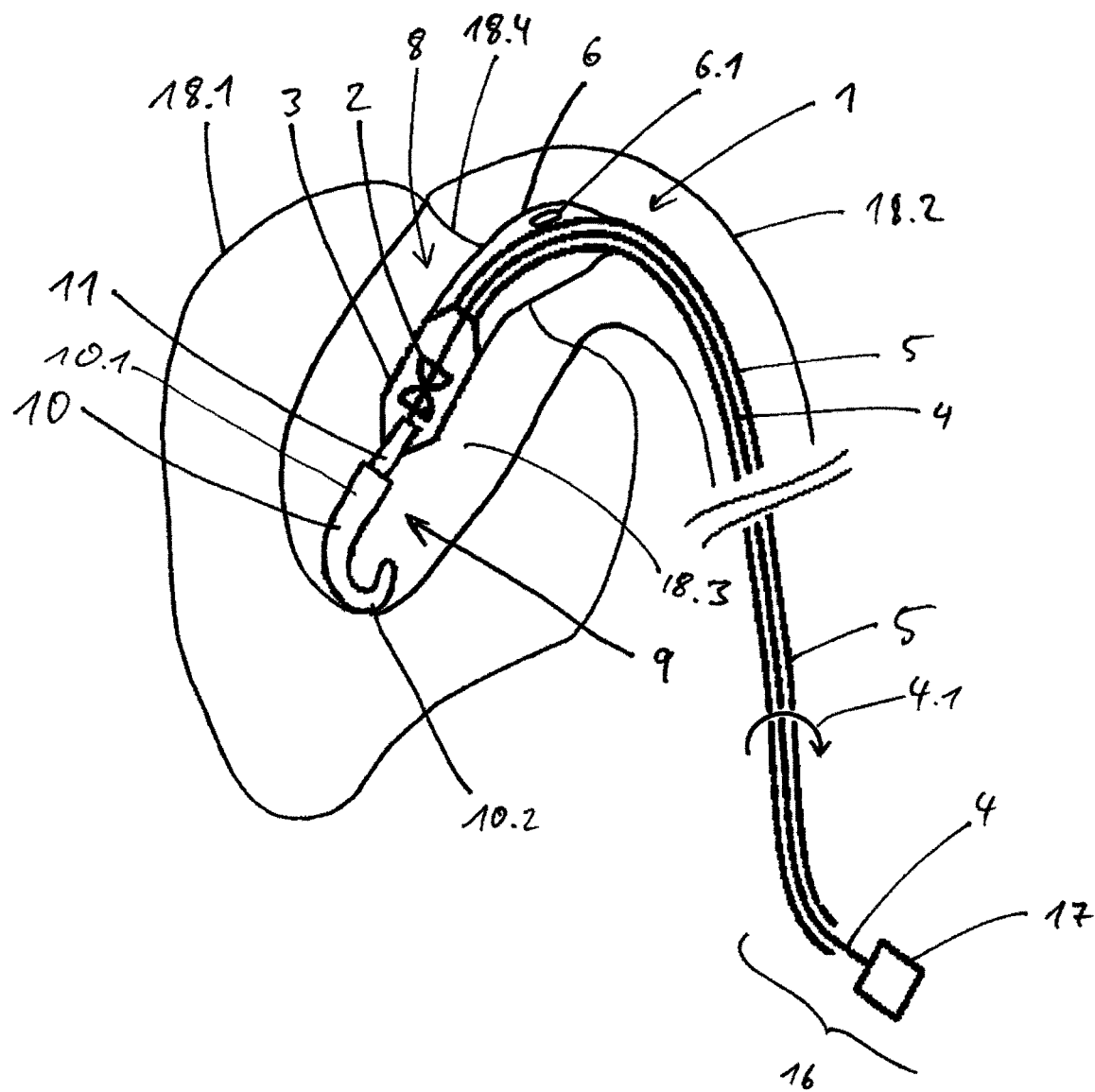
FIG. 1 shows a catheter device which is positioned within the left ventricle of a heart.

FIG. 1 shows a catheter device 1 used as a blood pump. The catheter device 1 is introduced into a patient, such that a portion of the distal end region 8 of the catheter device 1 is positioned within the left ventricle 18.3 of the heart 18.1 of the patient. In a driving region 16 which can lie outside of the patient's body, a motor 17 is provided for driving a drive shaft 4. A portion of the drive shaft 4 is covered by a pliable sheath 5. The drive shaft 4 and the pliable sheath 5 extend from the driving region 16 to the distal end region 8, where a rotor 2, preferably configured as a compressible rotor, is driven by the drive shaft 4. The compressible rotor 2 is located within a compressible housing 3. The compressibility of the rotor 2 and the housing 3 is useful for introducing the rotor into the patient's body. During operation, the rotor 2 and the housing 3 are in an expanded state. The housing 3 prevents damage to heart tissue such as for instance the tendinous chords, as it prevents tissue from being sucked into the rotor 2 or becoming entangled with the rotor 2 or the drive shaft 4. The distal end of the drive shaft 4 lies within a distal bearing 9. The distal bearing comprises a drive shaft cover 11 and a polymer end part 10, the polymer end part preferably made of a flexible material, such as Pebax® or another flexible medical grade polymer. The polymer end part comprises an elongated portion 10.1 which is provided around a part of the drive shaft cover 10. The polymer end part 10 further comprises a pigtail tip 10.2 to prevent damage to the heart 18.1. The rotor 2 and the drive shaft 4 can rotate in a rotating direction 4.1, such that a flow of blood away from the distal end, towards the proximal end is effected, i.e. a blood flow out of the left ventricle 18.3 into the aorta 18.2 and to other regions of the patient's body. A downstream tubing 6 is provided proximally of the rotor 2 and the rotor housing 3, which downstream tubing has a downstream opening 6.1 that lies proximally of the aortic valve 18.4, such that the blood passes the aortic valve within the downstream tubing 6 and can then stream into the aorta 18.2. The downstream tubing 6 is made of a flexible material, such that it can be compressed by the aortic valve 18.4 as the patient's heart 18.1 continues to pump.

Figure 2:
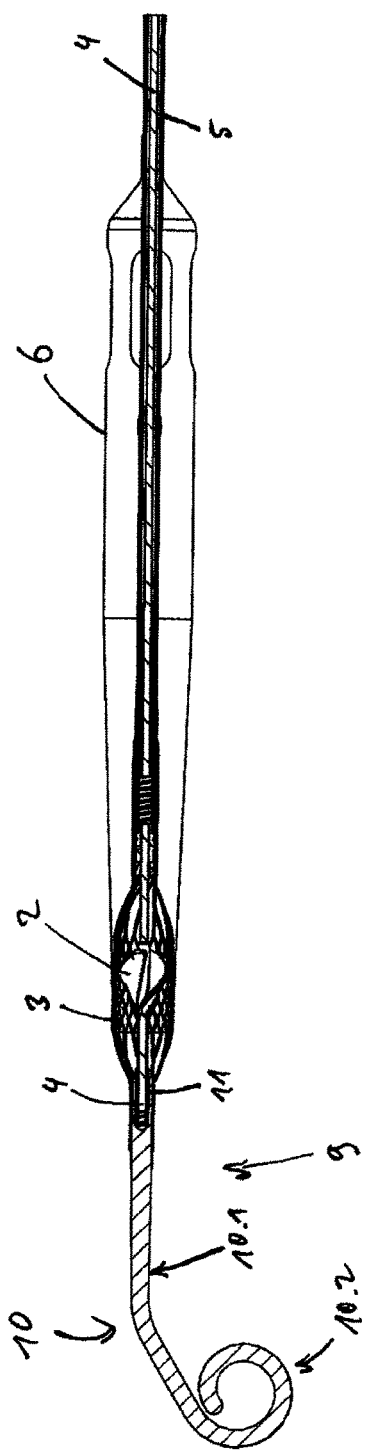
FIG. 2 shows the distal end region of a catheter device.

FIG. 2 shows a cut through the distal end region 8 of the catheter device 1. The distal bearing 9 comprises the polymer end part 10 with the pigtail 10.2 and the elongated portion 10.1. On the proximal end, the elongated portion 10.1 is provided around a portion of a drive shaft cover 11. The drive shaft 4 extends into the distal bearing 4 and is borne by the drive shaft cover 11. The rotor 2 lies close to the proximal side of the drive shaft over 11. The downstream tubing 6 is attached to the rotor housing 3 and extends proximally. The proximal end of the downstream tubing 6 is attached to the pliable sheath 5.

Figure 3:
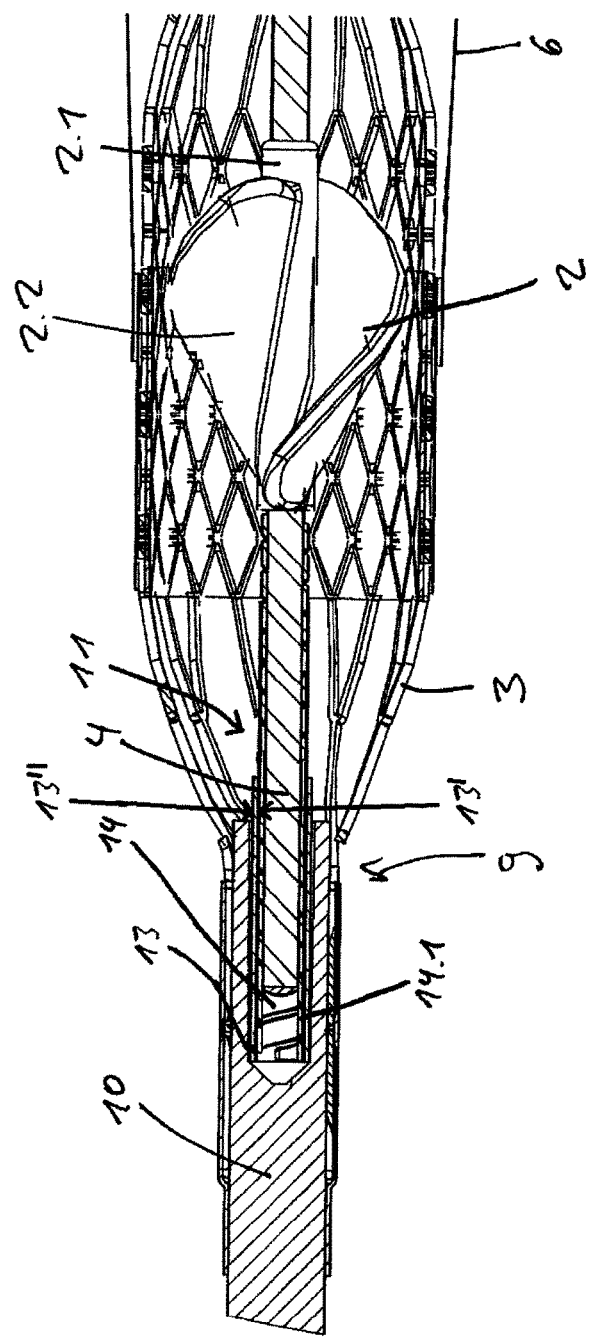
FIG. 3 shows an enlarged section of the distal end region of a catheter device.

FIG. 3 shows an enlarged portion of the end region 8 of the catheter device 1. In particular, the section of the distal bearing 9 which comprises the drive shaft cover 11 is shown. The drive shaft cover 11 extends from within the polymer end part 10, out of the polymer end part 10, into the rotor housing 3. The drive shaft 4 is made of one or more layers of coaxial windings which run spirally around a cavity extending axially at the center of the drive shaft. The winding direction of the coaxial windings can alternate from one layer to the next. This setup can improve the flexibility of the drive shaft. The outer diameter of the drive shaft lies in a range of about 0.4 to about 2 mm. Preferably, the outer diameter lies between 0.6 mm and 1.2 mm. Particularly preferably, the diameter lies between 0.8 mm and 1.0 mm. The drive shaft cover 11 is designed for bearing the drive shaft 4. It comprises a sleeve with a lumen in which the drive shaft 4 is inserted. The sleeve is preferably designed as a spiral sleeve 14 out of flat tape 14.1. The tape can for instance be made of MP35N® or 35NLT® or ceramics. The inner diameter of the spiral sleeve 14 is chosen such that the drive shaft 4 can be mounted but remains rotatable, while no large amounts of blood can enter the gap between the drive shaft 4 and the spiral sleeve 14. The inner diameter of the spiral sleeve 14 can for instance be chosen to be between 0.01 mm and 0.08 mm larger than the outer diameter of the drive shaft 4, preferably between 0.01 mm and 0.05 mm larger than the outer diameter of the drive shaft 4. The inner diameter of the spiral sleeve 14 is between 0.4 mm and 2.1 mm, preferably between 0.6 mm and 1.3 mm, particularly preferably between 0.8 mm and 1.1 mm. The thickness of the spiral sleeve 14 is between 0.05 mm and 0.4 mm. Such a spiral sleeve 14 provides flexibility, particularly in the region extending out of the polymer end part 10. Preferably, the flexibility of the drive shaft cover 11 is such that a kink in the drive shaft is avoided if the distal end region 8 of the catheter device 1 is bent. Furthermore, the flexibility of the drive shaft cover 11 is such that the drive shaft 4 remains centered within the housing 3 and the rotor 2 does not touch the housing 3. The proximal end of the spiral sleeve, preferably both ends of the spiral sleeve are face ground. Furthermore, the edges of the both ends of the spiral sleeve are rounded and smooth, preferably with a ten-point mean roughness of $R_z \leq 2$ μm, according to the ISO 1302 standard. The drive shaft cover 11 can further comprise a heat conducting part 13 which can be designed as a tube which is provided around a portion of the spiral sleeve 14. The heat conducting tube or part 13 is made of a material with a higher thermal conductivity than the polymer end part 10, in particular it can be made of medical grade stainless steel, such as 1.4441 stainless steel. The heat conducting part 13, when designed as a tube, is provided at least around a portion of the spiral sleeve 14 which lies inside the polymer end part 10, in some embodiments, the heat conducting part 13 or tube extends out of the polymer end part 10, into a region within the housing 3 which can be configured to be in direct contact with the blood of the patient. In particular, the heat conducting part 13 designed as a tube can extend between 0.5 mm and 2 mm out of the polymer end part 10, preferably between 1 mm and 1.5 mm. The heat conducting part 13 or tube can have a thickness of between 0.05 mm and 0.5 mm. An inner diameter of the heat conducting tube can be between 0.5 mm and 2.6 mm, preferably between 0.7 mm and 1.8 mm, particularly preferably between 0.9 mm and 1.6 mm. If the heat conducting part 13 or tube is configured such that a portion of the outer side 13" of the heat conducting part 13 or tube can be brought in direct contact with the blood of the patient, the area of the outer side (13") of the heat conducting part 13 or tube which can be brought in contact with the blood of the patient is preferably smooth, for instance with a ten-point mean roughness of $R_z \leq 1.2$ μm according to the ISO 1302 standard. The portion of the outer side 13" of the heat conducting part 13 which is configured to lie within the polymer end part and be in contact with the polymer end part is preferably roughened, for instance by laser texturing or knurling, preferably with an average surface roughness of $R_a \geq 0.8$ μm, according to the ISO 1302 standard. On the proximal side of the drive shaft cover 11, the rotor 2 with a rotor hub 2.1 is provided around the drive shaft 4. When in the operating state, in which the rotor is expanded, the rotor hub 2.1 is kept at a distance of between 0.2 mm and 0.7 mm from the drive shaft cover, preferably at a distance of between 0.25 mm and 0.4 mm. The hub 2.1 of the rotor is designed such that the rotor blades 2.2 can be brought close to the drive shaft cover 11. The hub 2.1 extends less than 0.5 mm past the rotor blades in distal direction, preferably, it extends less than 0.1 mm or not at all past the rotor blades in distal direction.

The heat conducting part (13), which can be designed as a tube, can be provided inside the polymer end part 10 independently from the spiral sleeve 14, for example if a different kind of bearing or no additional sleeve for bearing the drive shaft 4 is envisioned.

FIG. 4*a* shows a schematic of a section of the distal end region 8 of the catheter device 1. A portion of the spiral sleeve 14 extends out of the polymer end part 10. The inner side 13' of the heat conducting part is in direct contact with the spiral sleeve 14 and can be rough in order to facilitate gluing the spiral sleeve 14 to the inner side 13' of the heat conducting part 13. The bare portion of the spiral sleeve 14 extending out of the polymer end part 10 is highly flexible and follows even strong bending motion of the drive shaft 4 during operation. A portion of the heat conducting tube 13 also extends out of the polymer end part 10 to enable heat transfer. In this embodiment, heat is transferred from the heat conducting 13 tube directly to the blood. The heat conducting tube 13 can also extend further into the distal bearing 10 and cover the spiral sleeve 14 at least in all areas that lie inside the polymer end part 10. In an alternative embodiment, there is no heat conducting tube 13, but all other features are the same.

Figure 4B:
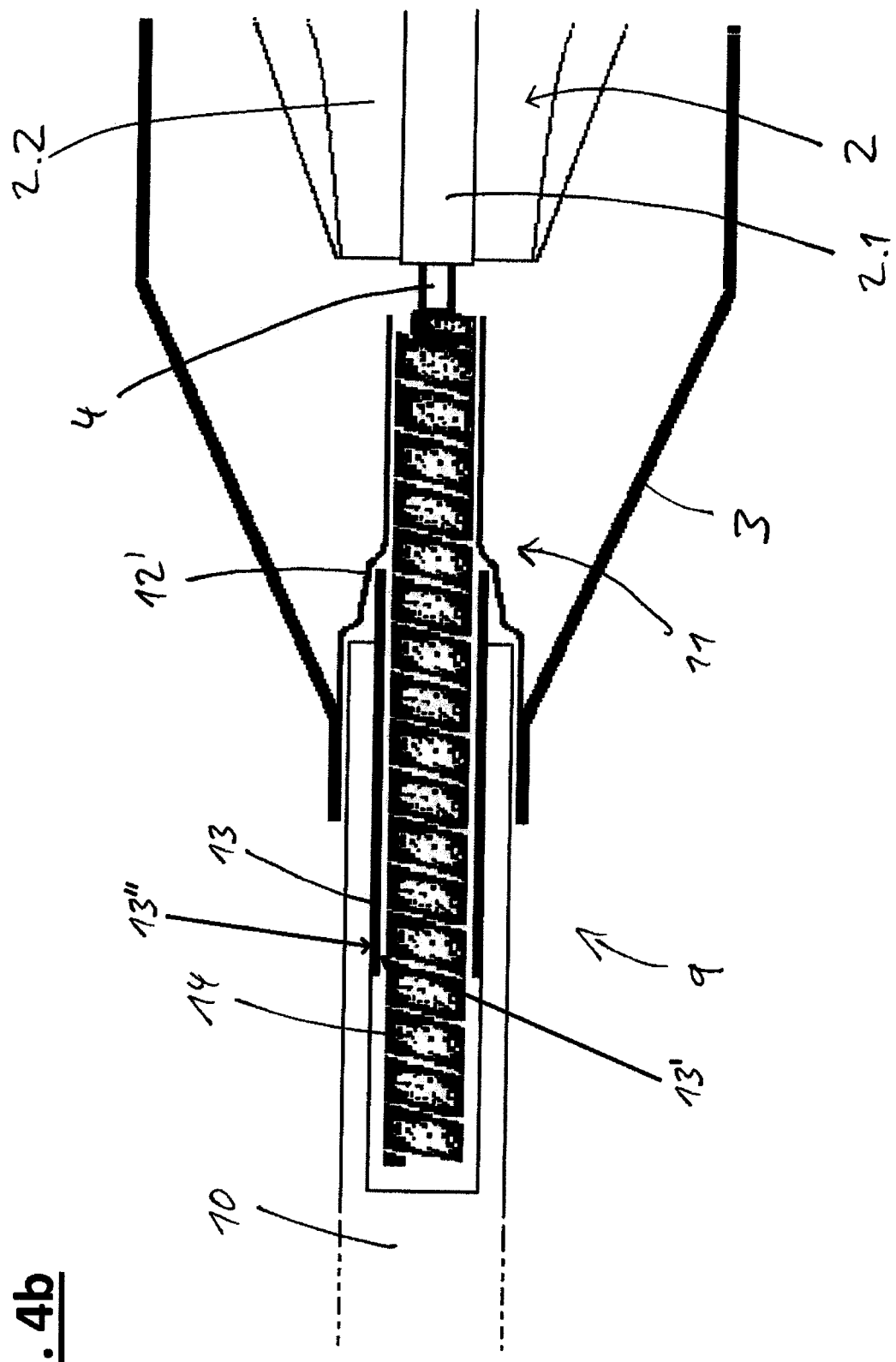

FIG. 4*b* shows a schematic of the same section of the distal end region 8 of the catheter device 1 as FIG. 4*a*. The drive shaft cover 11 further comprises a flexible tube 12' around the outside of the spiral sleeve or a portion of the outside of the spiral sleeve. In the embodiment shown in FIG. 4*b*, the flexible tube 12' runs around a proximal portion of the polymer end part 10, around a portion of the outer side 13" of the heat conducting part 13 which reaches out of the polymer end part 10, and around the portion of the spiral sleeve 14 extending out of the polymer end part 10. The inner side 13' of the heat conducting part is in direct contact with the spiral sleeve 14 and can be rough in order to facilitate gluing the spiral sleeve to the inner side 13' of the heat conducting part 13. The flexible tube can be implemented as a shrink hose and can be made for instance of silicone or of Pebax® or of PU or of PET. For good heat conductivity, the flexible tube can have a small wall thickness, for instance smaller than 0.2 mm, in particular smaller than 0.02 mm. In this embodiment, heat is transferred from the heat conducting 13 tube to the blood through the flexible tube 12'. In an embodiment featuring a flexible tube 12', rings made of flat tape can be provided on the inside of the flexible tube 12' instead of a spiral sleeve. They can for example be made of MP35N® or 35NLT® or ceramics and have the same thickness and inner diameter as the spiral sleeve. In a possible embodiment with rings, the rings are arranged distant from each other.

FIG. 5*a* shows the same section as FIG. 4*b*, but with a flexible tube 12" in a different configuration. The flexible tube 12" can also be implemented as a shrink hose and be made of for instance of silicone or of PEBAX®, PU or PET. For good heat conductivity, the flexible tube can have a small wall thickness, for instance smaller than 0.2 mm, in particular smaller than 0.02 mm. The flexible tube 12" is provided on the outside of the spiral sleeve 14, and it runs along the inner side 13' of the heat conducting part 13 or tube and inside the polymer end part 10. In the embodiment shown here, the flexible tube 12" extends all the way to the distal end of the spiral sleeve 14. In this configuration, a portion of the outer side 13" of the heat conducting part 13 is configured to be in direct contact with the blood of the patient upon insertion of the catheter device 1 into a patient. Said portion is smooth, for instance with a ten-point mean roughness $R_z$, according to the ISO 1302 standard, of $R_z \leq 1.2$ μm.

FIG. 5*b* shows a similar configuration as FIG. 5*a*, with the flexible tube 12" provided on the outside of the spiral sleeve 14, running on inner side (13') of the heat conducting part 13 and inside the polymer end part 10. Different from FIG. 5*a*, the flexible tube 12" does not extend all the way to the distal end of the spiral sleeve 14 such that a distal portion of the spiral sleeve is not covered by the flexible tube 12". The heat conducting part 13, on the other hand, extends further to the distal end of the spiral sleeve 14 and thus a portion of its inner side 13' is configured to be in direct contact with the spiral sleeve 14. In this configuration, said portion of the inner side 13' of the heat conducting part 13 can be glued to the outside of the spiral sleeve 14. It is advantageous to provide a roughened surface on the inner side 13' of the heat conducting part 13'. For instance, with an average surface roughness of $R_a \geq 0.8$ μm, according to the ISO 1302 standard. Furthermore, to enable the application of glue between the heat conducting part 13 and the spiral sleeve 14, the heat conducting 13 when designed as a tube can have an inner diameter which is between 0.04 mm and 0.1 mm larger than the outer diameter of the spiral sleeve 14.

FIG. 6 shows the spiral sleeve 14. The ends are face ground and smooth. The flat tape 14.1 is shown in a cut-away. The winding 14.2 has a winding direction from proximal to distal, which is the opposite direction of the preferred rotating direction 4.1 of the drive shaft 4, when looking in distal direction. This way, a rotating part cannot get damaged or caught by a pointed tip at the proximal end of the spiral sleeve 14.

FIG. 7 shows the rotor 2 and the housing 3 and a cannula 15 in two states a and b. The rotor 2 and the housing 3 are configured to be transferred into the cannula 15, for instance by exerting a force at the proximal end of the pliable sheath 5. When transferred into the cannula, the rotor 2' and the housing 3' are compressed in a radial direction, from their expanded states 2,3 into their compressed states 2',3'. The cannula 15 can be a cannula pertaining to the catheter device 1 or peel-away-sheath to aid the insertion of the catheter device 1 into the body of a patient. The housing 3 in the expanded state has a length 3.1. As the housing 3 is compressed to the compressed state 3', the length increases to a length 3.1'. As the length changes, the relative position of the distal bearing 9 which is attached to the housing 3 with respect to the drive shaft 4 changes. The drive shaft cover 11 is designed such that the distal end of the drive shaft 4 remains within the drive shaft cover 11 as the housing 3 undergoes changes in length.

The application further relates to the following aspects:
1. A catheter device (1), comprising:
   a rotor (2) located at the distal end region of the catheter device (1);
   a drive shaft (4) extending from a driving region (16) of the catheter device (1) to the distal end region (8) of the catheter device;

a distal bearing (9) for bearing a distal end of the drive shaft; and wherein the distal bearing (9) comprises a spiral sleeve (14) with a winding, configured for rotatably mounting the distal end of the drive shaft (4) inside the spiral sleeve (14).

2. A catheter device (1) according to aspect 1, characterized in that the spiral sleeve (14) is made of flat tape (14.1).
3. A catheter device (1) according to one of the preceding aspects, characterized in that the drive shaft (4) comprises a cavity extending axially with the drive shaft (4) and wherein the drive shaft (4) comprises a plurality of coaxial windings which run spirally around the cavity of the drive shaft (4), the windings within different coaxial layers having opposite winding directions, and in that the outer diameter of the drive shaft lies in a range of about 0.4 mm to about 2 mm, preferably comprising a reinforcement element which is provided sectionally in the cavity of the drive shaft (4) in the distal end region.
4. A catheter device (1) according to one of the preceding aspects, characterized in that both ends of the spiral sleeve (14) are face ground and all edges of both ends are rounded and smooth, preferably with a ten-point mean roughness of $R_z \le 2$ µm.
5. A catheter device according to one of the preceding aspects, characterized in that a flexible tube (12, 12') is provided around a portion of the outside of the spiral sleeve, wherein the flexible tube is preferably designed as a shrink hose.
6. A catheter device (4) according to one of the preceding aspects, wherein the rotor (2) and the drive shaft (4) are configured to rotate in a rotating direction (4.1) such that a proximally directed flow of fluid is effected, if the catheter device (1) is brought in contact with a fluid, characterized in that, when looking along the drive shaft (4) towards a distal end of the drive shaft, the winding direction of the spiral sleeve (14) from a proximal end of the spiral sleeve (14) to a distal end of the spiral sleeve (14), is the opposite direction of the rotating direction (4.1) of the rotor (2) and the drive shaft (4), when looking along the drive shaft towards a distal end of the drive shaft.
7. A catheter device (1) according to one of the preceding aspects, characterized in that the spiral sleeve (14) is made out of MP35N®, 35NLT®, or ceramics.
8. A catheter device (1) according to one of the preceding aspects, characterized in that an inner diameter of the spiral sleeve (14) is between 0.4 mm and 2.1 mm and in that the spiral sleeve has a thickness between 0.05 mm to 0.4 mm.
9. A catheter device (1) according to one of the preceding aspects, characterized in that the spiral sleeve (14) and/or the flexible tube (12,12'), if a flexible tube according to one of the aspects 5 to 8 is provided, is at least in part in contact with a heat conducting part (13), the heat conducting part (13) being configured to enable heat transfer away from the distal bearing (9) and/or the spiral sleeve (14).
10. A catheter device according to aspect 9, characterized in that the heat conducting part (13) is designed as a tube surrounding a portion of the spiral sleeve (14).
11. A catheter device according to one of the aspects 9 or 10, characterized in that the heat conducting part or tube (13) extends out of the distal bearing, into an area which is configured to be brought in contact with a fluid, enabling heat transfer from the distal bearing (9) to the fluid.
12. A catheter device (1) according to one of the preceding aspects, characterized in that the distal bearing (9) comprises a polymer end part (10) or the distal bearing (9) comprises a polymer end part which comprises a region which is designed as a pigtail (10.2).
13. A catheter device (1) according to one of the aspects 9 to 12, characterized in that a portion of the outer side (13") of the heat conducting part (13) which is configured to be brought in contact with the fluid is smooth, preferably with a ten-point mean roughness of $R_z \le 1.2$ µm, and in that an inner side (13') of the heat conducting part (13) is rough to facilitate gluing the spiral sleeve (14) to the inner side (13') of the heat conducting part (13), the inner side (13') of the heat conducting part or tube (13) preferably having an arithmetic average surface roughness of $R_a \ge 0.8$ µm.
14. A catheter device according to aspect 13, characterized in that a further portion of the outer side (13") of the heat conducting part or tube (13) which is configured to lie inside the polymer end part is roughened, preferably having an arithmetic average surface roughness of $R_a \ge 0.8$ µm.
15. A catheter device according to one of the aspects 9 to 14, characterized in that an inner diameter of the heat conducting part (13) designed as a tube is between 0.5 mm and 2.6 mm and/or in that the heat conducting part has a thickness between 0.05 mm and 0.5 mm.
16. A catheter device according to one of the aspects 9 to 15, characterized in that the heat conducting part (13) is made of a medical grade stainless steel, preferably made of 1.4441 stainless steel.
17. A catheter device (1) according to one of the preceding aspects, designed as an expandable pump, characterized in that a cannula is provided around a portion of the drive shaft (4) which lies in the vicinity of the rotor (2) and in that the rotor (2) is located in a housing (3), the housing (3) and the rotor (2) being configured to be transferred at least in part into the cannula (15), wherein the housing (3) and the rotor (2) are compressed at least along a radial direction extending transversely to a longitudinal direction, from an expanded state into a compressed state.
18. A catheter device (1) according to one of the preceding aspects, wherein, upon application of a force at the proximal end of the catheter and/or compression of the housing and the rotor, a relative motion of the drive shaft (4) with respect to the distal bearing (9) is effected, and wherein the drive shaft and the distal bearing are configured such that the distal end of the drive shaft remains within the spiral sleeve (14) when the housing (3) and the rotor (2) are compressed.
19. A catheter device (1) according to one of the preceding aspects, characterized in that a hub (2.1) pertaining to the rotor (2) extends less than 0.5 mm past the rotor blades (2.2) towards the distal end of the catheter device, preferably less than 0.1 mm.

LIST OF REFERENCE NUMERALS

1 Catheter Device
2 Rotor
2' Rotor (compressed state)
2.1 Hub
2.2 Rotor blade

3 Housing
3' Housing (compressed state)
3.1 Length of the housing
3.1' Length of the housing (compressed state)
4 Drive shaft
4.1 Rotating direction of the drive shaft
5 Pliable Sheath
6 Downstream tubing
6.1 Downstream opening
8 Distal end region
9 Distal bearing
10 Polymer end part
10.1 Elongated portion of the polymer end part
10.2 Pigtail
11 Drive shaft cover
12' Flexible tube (outside configuration)
12" Flexible tube (inside configuration)
13 Heat conducting part
13' Inner side of the heat conducting part
13" Outer side of the heat conducting part
14 Spiral sleeve
14.1 Flat tape
14.2 Winding of the spiral sleeve
15 Cannula
16 Driving region
17 Motor
18.1 Heart
18.2 Aorta
18.3 Left ventricle
18.4 Aortic valve

The invention claimed is:

1. A catheter device, comprising:
   a rotor located at a distal end region of the catheter device;
   a drive shaft extending from a driving region of the catheter device to the distal end region of the catheter device;
   a distal bearing located at a distal end of the rotor for bearing a distal end of the drive shaft, the distal bearing comprising a spiral sleeve with a winding and configured for rotatably mounting the distal end of the drive shaft inside the spiral sleeve; and
   wherein the distal bearing comprises a heat conducting part configured to enable heat transfer away from the distal bearing,
   wherein the spiral sleeve with the winding is arranged within the distal bearing, such that a portion of the spiral sleeve and a portion of the heat conducting part are only separated by a thin flexible tube which is provided around a portion of an outside of the spiral sleeve.

2. The catheter device according to claim 1, wherein the heat conducting part is designed as a tube surrounding the drive shaft.

3. The catheter device according to claim 1, wherein the drive shaft further comprises:
   a cavity extending axially with the drive shaft and wherein the drive shaft comprises a plurality of coaxial windings which run spirally around the cavity of the drive shaft, the windings within different coaxial layers having opposite winding directions and in that an outer diameter of the drive shaft lies in a range of about 0.4 mm to about 2 mm.

4. The catheter device according to claim 1, wherein the heat conducting part extends out of the distal bearing and into an area which is configured to be brought in contact with a fluid, enabling heat transfer from the distal bearing to the fluid.

5. The catheter device according to claim 1, wherein the distal bearing further comprises a polymer end part or the distal bearing comprises a polymer end part which comprises a region which is designed as a pigtail.

6. The catheter device according to claim 1, wherein the heat conducting part is made of a medical grade stainless steel.

7. The catheter device according to claim 1, wherein an inner diameter of the heat conducting part is between 0.5 mm and 2.6 mm or in that the heat conducting part has a thickness between 0.05 mm and 0.5 mm.

8. The catheter device according to claim 1, wherein the spiral sleeve with the winding is arranged within the distal bearing, for rotatably mounting a distal end of the drive shaft inside the spiral sleeve, such that the spiral sleeve lies at least in part inside the heat conducting part designed as a tube or such that a portion of the spiral sleeve is in direct contact with a portion of an inner side of the heat conducting part.

9. The catheter device according to claim 8, wherein the spiral sleeve is made of flat tape.

10. The catheter device according to claim 1, wherein a portion of an outer side of the heat conducting part which is configured to be brought in contact with a fluid is smooth and in that an inner side of the heat conducting part is rough to facilitate gluing the spiral sleeve to the inner side of the heat conducting part.

11. The catheter device according to claim 10, wherein a further portion of the outer side of the heat conducting part or tube, which is configured to lie inside a polymer end part, is roughened.

12. The catheter device according to claim 8, wherein both ends of the spiral sleeve are face ground and all edges of both ends are rounded and smooth.

13. The catheter device according to claim 8, wherein an inner diameter of the spiral sleeve is between 0.4 mm and 2.1 mm, and in that the spiral sleeve has a thickness between 0.05 mm to 0.4 mm.

14. The catheter device according to claim 8, wherein the rotor and the drive shaft are configured to rotate in a rotating direction such that a flow of fluid in a proximal direction is effected, if the catheter device is brought in contact with a fluid, and further wherein, when looking along the drive shaft towards a distal end of the drive shaft, the winding direction of the spiral sleeve from a proximal end of the spiral sleeve to a distal end of the spiral sleeve, is the opposite direction of the rotating direction of the rotor and the drive shaft, when looking along the drive shaft towards a distal end of the drive shaft.

15. The catheter device according to claim 8, wherein the spiral sleeve is made out of metal or ceramics.

16. The catheter device according to claim 1, designed as an expandable pump, wherein a cannula is provided around a portion of the drive shaft which lies in a vicinity of the rotor and in that the rotor is located in a housing, the housing and the rotor being configured to be transferred at least in part into the cannula, wherein the housing and the rotor are compressed at least along a radial direction extending transversely to a longitudinal direction, from an expanded state into a compressed state.

17. The catheter device according to claim 16, wherein, upon application of a force at a proximal end of a catheter or compression of the housing and the rotor, a relative motion of the drive shaft with respect to the distal bearing is effected, and wherein the drive shaft and the distal bearing are configured such that a distal end of the drive shaft remains within the distal bearing or within the heat conducting part designed as a tube or within the spiral sleeve when the housing and the rotor are compressed.

18. The catheter device according to claim 1, wherein a hub pertaining to the rotor extends less than 0.5 mm past rotor blades of the rotor towards a distal end of the catheter device.

19. A catheter device, comprising:
a rotor located at a distal end region of the catheter device;
a drive shaft extending from a driving region of the catheter device to the distal end region of the catheter device;
a distal bearing located at a distal end of the rotor for bearing a distal end of the drive shaft; and
wherein the distal bearing comprises a heat conducting part and a spiral sleeve with a winding,
wherein the spiral sleeve with the winding is arranged within the distal bearing, such that a portion of the spiral sleeve and a portion of the heat conducting part are only separated by a thin flexible tube which is provided around a portion of an outside of the spiral sleeve.

20. The catheter device according to claim 19, wherein the spiral sleeve is made of flat tape.

21. The catheter device according to claim 19, wherein the drive shaft comprises a cavity extending axially with the drive shaft and wherein the drive shaft comprises a plurality of coaxial windings which run spirally around the cavity of the drive shaft, the windings within different coaxial layers having opposite winding directions and in that an outer diameter of the drive shaft lies in a range of about 0.4 mm to about 2 mm.

22. The catheter device according to claim 19, wherein both ends of the spiral sleeve are face ground and all edges of both ends are rounded and smooth.

23. The catheter device according to claim 19, wherein the flexible tube is provided around a portion of an outside of the spiral sleeve.

24. The catheter device according to claim 19, wherein the rotor and the drive shaft are configured to rotate in a rotating direction such that a proximally directed flow of fluid is effected, if the catheter device is brought in contact with a fluid, and further wherein, when looking along the drive shaft towards a distal end of the drive shaft, the winding direction of the spiral sleeve from a proximal end of the spiral sleeve to a distal end of the spiral sleeve, is the opposite direction of the rotating direction of the rotor and the drive shaft, when looking along the drive shaft towards a distal end of the drive shaft.

25. The catheter device according to claim 19, wherein the spiral sleeve is made out of metal or ceramics.

26. The catheter device according to claim 19, wherein an inner diameter of the spiral sleeve is between 0.4 mm and 2.1 mm and in that the spiral sleeve has a thickness between 0.05 mm to 0.4 mm.

27. The catheter device according to claim 19, wherein the spiral sleeve or the flexible tube is at least in part in contact with the heat conducting part, the heat conducting part being configured to enable heat transfer away from the distal bearing or the spiral sleeve.

28. The catheter device according to claim 27, wherein the heat conducting part is designed as a tube surrounding a portion of the spiral sleeve.

29. The catheter device according to claim 27, wherein the heat conducting part or tube extends out of the distal bearing and into an area which is configured to be brought in contact with a fluid, enabling heat transfer from the distal bearing to the fluid.

30. The catheter device according to claim 19, wherein the distal bearing comprises a polymer end part or the distal bearing comprises a polymer end part which comprises a region which is designed as a pigtail.

31. The catheter device according to claim 27, wherein a portion of an outer side of the heat conducting part which is configured to be brought in contact with a fluid is smooth, and in that an inner side of the heat conducting part is rough to facilitate gluing the spiral sleeve to the inner side of the heat conducting part.

32. The catheter device according to claim 31, wherein a further portion of the outer side of the heat conducting part or tube which is configured to lie inside a polymer end part is roughened.

33. The catheter device according to claim 27, wherein an inner diameter of the heat conducting part designed as a tube is between 0.5 mm and 2.6 mm or in that the heat conducting part has a thickness between 0.05 mm and 0.5 mm.

34. The catheter device according to claim 27, wherein the heat conducting part is made of a medical grade stainless steel.

35. The catheter device according to claim 19, designed as an expandable pump, wherein a cannula is provided around a portion of the drive shaft which lies in a vicinity of the rotor and in that the rotor is located in a housing, the housing and the rotor being configured to be transferred at least in part into the cannula, and further wherein the housing and the rotor are compressed at least along a radial direction extending transversely to a longitudinal direction, from an expanded state into a compressed state.

36. The catheter device according to claim 19, wherein, upon application of a force at a proximal end of a catheter or compression of a housing and the rotor, a relative motion of the drive shaft with respect to the distal bearing is effected, and further wherein the drive shaft and the distal bearing are configured such that a distal end of the drive shaft remains within the spiral sleeve when the housing and the rotor are compressed.

37. The catheter device according to claim 19, wherein a hub pertaining to the rotor extends less than 0.5 mm past rotor blades of the rotor towards the distal end of the catheter device.

38. A catheter device, comprising:
a rotor located at a distal end region of the catheter device;
a drive shaft extending from a driving region of the catheter device to the distal end region of the catheter device;
a distal bearing located at a distal end of the rotor for bearing a distal end of the drive shaft;
wherein the distal bearing comprises a spiral sleeve with a winding, configured for rotatably mounting the distal end of the drive shaft inside the spiral sleeve,
wherein the spiral sleeve, which is provided around a portion of an outside of the spiral sleeve, is at least in part in contact, with a heat conducting part, the heat conducting part being configured to enable heat transfer away from the distal bearing or the spiral sleeve, and
wherein the spiral sleeve with the winding is arranged within the distal bearing, such that a portion of the spiral sleeve and a portion of the heat conducting part are only separated by a thin flexible tube which is provided around a portion of an outside of the spiral sleeve.

39. The catheter device according to claim 3, wherein the drive shaft further comprises a reinforcement element which is provided sectionally in the cavity of the drive shaft in the distal end region of the catheter device.

40. The catheter device according to claim 6, wherein the heat conducting part is made of 1.4441 stainless steel.

41. The catheter device according to claim 1, wherein the flexible tube is designed as a shrink hose.

42. The catheter device according to claim 10, wherein the inner side of the heat conducting part or tube is configured to have an arithmetic average surface area roughness of $R_a \geq 0.8$ μm and the portion of the outer side of the heat conducting part has a ten-point mean roughness of $R_z \leq 1.2$ μm.

43. The catheter device according to claim 11, wherein the further portion of the outer side of the heat conducting part or tube is configured to have an arithmetic average surface area roughness of $R_a \geq 0.8$ μm.

44. The catheter device according to claim 12, wherein all edges of both ends of the spiral sleeve are rounded and smooth with a ten-point mean roughness of $R_z \leq 2$ μm.

45. The catheter device according to claim 18, wherein the hub pertaining to the rotor extends less than 0.1 mm past the rotor blades towards the distal end of the catheter device.

46. The catheter device according to claim 21, wherein the drive shaft further comprises a reinforcement element which is provided sectionally in the cavity of the drive shaft in the distal end region of the catheter device.

47. The catheter device according to claim 22, wherein all edges of both ends of the spiral sleeve are rounded and smooth with a ten-point mean roughness of $R_z \leq 2$ μm.

48. The catheter device according to claim 23, wherein the flexible tube is designed as a shrink hose.

49. The catheter device according to claim 31, wherein the portion of the outer side of the heat conducting part has a ten-point mean roughness of $R_z \leq 1.2$ μm and the inner side of the heat conducting part or tube has an arithmetic average surface roughness of $R_a \leq 0.8$ μm.

50. The catheter device according to claim 32, wherein the further portion of the outer side of the heat conducting part or tube has an arithmetic average surface roughness of $R_a \leq 0.8$ μm.

51. The catheter device according to claim 34, wherein the heat conducting part is made of 1.4441 stainless steel.

52. The catheter device according to claim 37, wherein the hub pertaining to the rotor extends less than 0.1 mm past the rotor blades towards the distal end of the catheter device.

* * * * *